(12) United States Patent
Ullberg

(10) Patent No.: US 8,774,354 B2
(45) Date of Patent: Jul. 8, 2014

(54) COMPUTED TOMOGRAPHY SCANNING SYSTEM AND METHOD

(75) Inventor: Christer Ullberg, Sollentuna (SE)

(73) Assignee: Xcounter AB, Danderyd (SE)

( * ) Notice: Subject to any disclaimer, the term of this patent is extended or adjusted under 35 U.S.C. 154(b) by 371 days.

(21) Appl. No.: 13/182,799

(22) Filed: Jul. 14, 2011

(65) Prior Publication Data

US 2012/0014503 A1    Jan. 19, 2012

Related U.S. Application Data

(60) Provisional application No. 61/364,076, filed on Jul. 14, 2010.

(30) Foreign Application Priority Data

Jul. 14, 2010  (SE) ...................................... 1050794

(51) Int. Cl.
*G01T 1/105* (2006.01)
*G01N 23/083* (2006.01)
*H05G 1/38* (2006.01)

(52) U.S. Cl.
USPC ............... 378/19; 378/37; 378/197; 378/901; 250/584; 250/491.1

(58) Field of Classification Search
USPC ............ 378/4–20, 37, 62, 91, 98, 98.12, 145, 378/193, 197, 204, 210, 901; 250/580–587, 250/370.01, 370.08, 370.09, 370.13, 371, 250/491.1, 526

See application file for complete search history.

(56) References Cited

U.S. PATENT DOCUMENTS 3,784,820 A    1/1974  Miraldi
4,314,275 A    2/1982  Chapman
(Continued)

FOREIGN PATENT DOCUMENTS

WO    WO 2009/122328 A1    10/2009

OTHER PUBLICATIONS

European Search Report Corresponding to Application No. 11173533.8; Dated Oct. 19, 2011; 8 pages.

(Continued)

*Primary Examiner* — Anastasia Midkiff
(74) *Attorney, Agent, or Firm* — Myers Bigel Sibley & Sajovec, PA

(57) ABSTRACT

A system for recording computed tomography image data of an object in an object area comprises an X-ray source and an X-ray detector arranged at either side of the object area, the X-ray source having a flying focal spot from which X-rays is emitted and the X-ray detector comprising pixels arranged in at least one row for recording images of the object. A device is provided for rotating the X-ray source and the X-ray detector with respect to the object around an axis of rotation, while the at least one row of pixels record images of the object. The X-ray source comprises means for moving the flying focal spot of the X-ray source from an original position and in a direction essentially opposite to the direction the X-ray source moves during the rotation, and the X-ray detector is provided with means for time delay summation such that pixel signal values of the at least one row of pixels are shifted one pixel and summed with pixel signal values obtained in a following recording of an image, wherein the shifting and summing of pixel signal values are performed repeatedly and the pixel signal values are shifted in a direction essentially opposite to the direction the X-ray detector moves during the rotation.

17 Claims, 3 Drawing Sheets

(56) References Cited

U.S. PATENT DOCUMENTS

| | | |
|---|---|---|
| 4,817,123 A | 3/1989 | Sones et al. |
| 5,173,852 A | 12/1992 | Lonn |
| 5,361,291 A | 11/1994 | Toth et al. |
| 5,379,336 A | 1/1995 | Kramer et al. |
| 5,590,164 A | 12/1996 | Kawai et al. |
| 5,768,331 A | 6/1998 | Gordon et al. |
| 5,841,829 A | 11/1998 | Dolazza et al. |
| 6,256,369 B1 | 7/2001 | Lai |
| 6,933,505 B2 | 8/2005 | Vuorela |
| 7,170,062 B2 | 1/2007 | Vuorela |
| 7,189,971 B2 | 3/2007 | Spartiotis et al. |
| 7,268,814 B1 | 9/2007 | Pain et al. |
| 7,361,881 B2 | 4/2008 | Spartiotis |
| 2004/0000630 A1 | 1/2004 | Spartiotis et al. |
| 2004/0081279 A1 | 4/2004 | Brunnett |
| 2006/0011853 A1 | 1/2006 | Spartiotis et al. |
| 2006/0071174 A1 | 4/2006 | Spartiotis et al. |
| 2006/0078084 A1 | 4/2006 | Souchay et al. |
| 2008/0019477 A1 | 1/2008 | Spartiotis et al. |
| 2009/0147919 A1 | 6/2009 | Goto et al. |
| 2009/0185655 A1 | 7/2009 | Koken et al. |
| 2010/0034344 A1 | 2/2010 | Hein et al. |
| 2010/0150305 A1 | 6/2010 | Nowak et al. |

OTHER PUBLICATIONS

International/Type Search Report for PCT/SE1050794-5, dated Jul. 14, 2010.

COMPUTED TOMOGRAPHY SCANNING SYSTEM AND METHOD

RELATED APPLICATIONS

The present application claims priority from Swedish Patent Application No. 1050794-5, filed Jul. 14, 2010, from U.S. Provisional Application No. 61/364,076, filed Jul. 14, 2010, the disclosures of each of which are hereby incorporated herein by reference in their entireties.

FIELD OF THE INVENTION

The present invention relates to the field of X-ray imaging, and in particular to a computed tomography scanning system and method for recording computed tomography image data of an object.

BACKGROUND

Computed tomography scanning (CT scanning), also denoted computerized tomography or computed axial tomography (CAT), is an imaging method employing imaging by sectioning or 3D reconstruction. In the CT-scanning an X-ray source and an X-ray detector are arranged opposite one another on an arrangement that rotates around an object. The X-ray source transmits radiation through the object and the X-ray detector measures the attenuated radiation. The radiation is converted to an electrical signal, a computer processes these signals and the desired images can be provided.

An important improvement of the two-dimensional scanning was made with the introduction of the so-called spiral or helical scan. Instead of scanning the object on a two-dimensional basis, the object is scanned on a three-dimensional basis. In particular, the table on which the object rests moves through the scanning field at a constant speed while the X-ray tube and X-ray detector rotates around the object. Digital geometry processing is used to generate a three-dimensional image of the internals of an object from a large series of two-dimensional X-ray images taken around a single axis of rotation.

SUMMARY OF EMBODIMENTS OF THE INVENTION

CT systems of today use rather narrow detectors with a small field of view in the translation direction. The detector is typically only 0.5-30 mm wide. There is a desire in CT imaging to make the detector wider in order to reduce the number of revolutions needed to image the organ or object of interest. The existing CT detectors use light sensitive CMOS detectors with scintillators emitting light when struck by X-rays. This detector technology cannot be used for implementing wide detectors due to the high costs and problems to read out the signals from a wider detector. An alternative being investigated is the use of area detectors. These area detectors are made of for example thin film transistor (TFT) panels. Such TFT-panels are currently used for 2D X-ray imaging.

However, the TFT-panels are slow to read out and can at most be read out 60 times per second, but then with rather large pixel size. Small pixel sizes can typically only be read out 5-10 times per second. This is far too slow for CT applications when one wishes to read out the detector one thousand times per revolution or more.

It would be desirable to provide CT-scanning in which a larger number of images could be taken without degrading the image quality, more specifically somewhere between 100 and 5000 images in each rotation of the X-ray arrangement, when rotating 0.1-1 revolutions per second. This would set high demands on the detector, for example in terms of readout speed. The detector would have to be able to rapidly detect radiation transmitted from the X-ray source and to quickly transfer the data from the detector to a buffer memory or to a computer from each readout. Further, in order to obtain usable images, that is, images having a high enough resolution, the size of the pixels have to be small, preferably within the range of 0.05-0.1 mm. The detectors used in CT-scanning today cannot meet these demands; they are simply not fast enough to take such high-resolution images at the required speed.

It is therefore an object of the invention to provide a computed tomography scanning system and method for recording computed tomography image data that overcome, or at least alleviate, the shortcomings of the prior art. In particular, an object is to provide a computed tomography scanning system and method wherein an increased quality of images recorded can be provided, while still enabling the imaging procedure to be performed quickly.

It is another object of the invention to increase the quality in terms of resolution and noise levels of the images recorded, thereby increasing the quality of a conclusion drawn, or a diagnosis made, based on the images.

These objects, among others, are achieved by systems and methods as claimed in the appended patent claims.

According to a first aspect of the present invention a system for recording computed tomography image data of an object in an object area is provided. The system comprises an X-ray source and an X-ray detector arranged at either side of the object area, wherein the X-ray source has a flying focal spot from which X-rays is emitted and the X-ray detector comprises pixels arranged in at least one row for recording images of the object. A device is provided for rotating the X-ray source and the X-ray detector with respect to the object, while the at least one row of pixels record images of the object. The X-ray source comprises means for moving the flying focal spot of the X-ray source from an original position and in a direction essentially opposite to the direction the X-ray source moves during the rotation, and the X-ray detector is provided with means for time delay summation such that pixel signal values of the at least one row of pixels are shifted one pixel and summed with pixel signal values obtained in a following recording of an image, wherein the shifting and summing of pixel signal values are performed repeatedly and the pixel signal values are shifted in a direction essentially opposite to the direction the X-ray detector moves during the rotation.

Preferably, the computed tomography image data are recorded during a session comprising first longer recording periods and second shorter readout periods, wherein each first longer recording period is followed by a shorter second readout period.

The rotating device is then provided for rotating the X-ray source and the X-ray detector at a certain rotational speed during the first longer recording periods and second shorter readout periods.

During each first longer recording period the flying focal spot moving means is provided for moving the flying focal spot at a selected speed which is essentially equal to the circumferential speed of the X-ray source due to the rotation by the rotating device. This means that the flying focal spot is "hovering" in a fixed position in space during each first longer recording period. Similarly, the time delay summation means is provided for shifting pixel signal values at a selected frequency, wherein the length of the pixels in the direction of the row of pixels divided by the selected frequency of the shifting is essentially equal to the circumferential speed of the X-ray detector due to the rotation by the rotating device. Hereby, the pixel signal values are shifted with same speed as the X-ray detector moves and the summation of pixel values results in that the X-ray detector emulates an X-ray detector that is held still in space during each first longer recording period.

During each second shorter readout period the flying focal spot moving means is provided for moving the flying focal spot back to its original position and the X-ray detector is provided for reading out the shifted and summed pixel signal values.

Hereby, a system for recording computed tomography image data is obtained which allows for high speed rotation of the X-ray source and the X-ray detector such that a large angular ranges can be covered in short time. Simultaneously, high spatial resolution and high signal to noise levels can be obtained. The invention thus provided for improved computed tomography measurements as compared with the prior art.

According to a second aspect of the invention there is provided a method for recording computed tomography image data of an object by the computed tomography scanning system of the first aspect of the invention. According to the method the X-ray source and the X-ray detector are rotated with respect to the object, while (i) images of the object are recorded by the at least one row of pixels, (ii) the flying focal spot of the X-ray source is moved from an original position and in a direction essentially opposite to the direction the X-ray source moves during the rotation, and (iii) pixel signal values of the at least one row of pixels are shifted one pixel and summed with pixel signal values obtained in a following recording of an image, wherein the shifting and summing of pixel signal values are performed repeatedly and the pixel signal values are shifted in a direction essentially opposite to the direction the X-ray detector moves during the rotation.

Further characteristics of the invention and advantages thereof will be evident from the detailed description of a preferred embodiment of the present invention given hereinafter and the accompanying drawings, which are only given by way of illustration, and thus are not limitative of the present invention.

DETAILED DESCRIPTION OF EMBODIMENTS

In the following the present invention is described and exemplified by means of a particular medical application, namely mammography. The invention is however applicable in other medical areas as well as in other areas, such as baggage checking and material testing, with suitable modifications.

Figure 1:
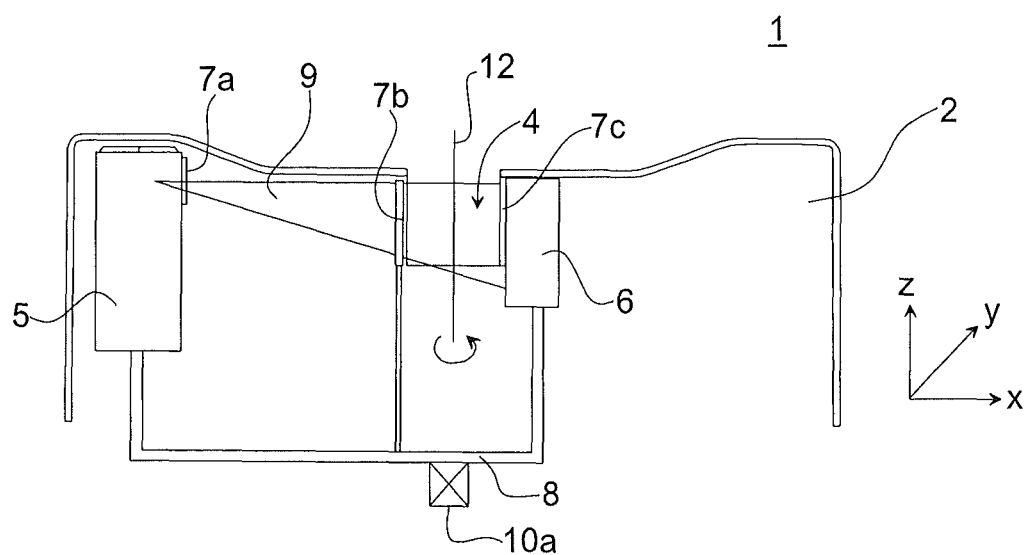
FIG. 1 illustrates schematically, in a side view, a computed tomography scanning system according to an embodiment of the invention.

FIG. 1 illustrates schematically, in a side view, a computed tomography scanning system for mammography applications according to an embodiment of the invention. A computed tomography scanning system 1 for medical imaging comprises a horizontally arranged patient positioning table 2 on which a patient may rest face down. The patient thereby rests comfortably on a horizontal examination table during the whole examination. The patient positioning table 2 comprises a suitably located opening 4 in which the patient places her breasts.

An imaging arrangement is provided underneath the patient positioning table 2. The imaging arrangement comprises an X-ray source 5, collimators 7a-c, and an X-ray detector 6 attached to a support device 8, for example a common E-arm. The support device 8 is illustrated very schematically in the Figure and it is realized that any suitable support structure may be utilized. The X-ray source 5 and the X-ray detector 6 are arranged on the support device 8 on opposite sides of the object to be imaged, the object being, in the illustrated example, the breast of a patient. The X-ray detector 6 is thereby able to measure the radiation emitted by the X-ray source 5 and transmitted through the breast of the patient. Typically the distance between the X-ray source 5 and the X-ray detector 6 is about 400 mm with the hole 4 located at half way between them.

The collimators 7a-c may each be a thin foil of e.g. tungsten with suitable openings. The collimators 7a-b prevents radiation, which is not directed directly towards the X-ray detector 6, from impinging on the object, thereby reducing the radiation dose to the object. This is advantageous in particular in all applications where the object is a human or an animal, or parts thereof. The downstream collimator 7c may reduce scattered radiation from striking the X-ray detector 6.

The imaging arrangement, that is, the support device 8 comprising the X-ray source 5, the collimators 7a-c, and the X-ray detector 6 is rotated with respect to the object to be imaged by means of a rotating device 10a, e.g. a rotational motor device, while the X-ray detector 6 records images of the object repeatedly by means of detecting radiation from the X-ray source 5 after having been attenuated by the object. The object, i.e. the breast, hangs down in a vertical direction while being imaged. There is no need to compress the breast but the breast should be held still during the procedure. The rotation axis of the imaging arrangement is vertical along the z axis through the breast and is indicated at 12. It may be located half way between the X-ray source 5 and the X-ray detector 6. The rotating device 10a may also be arranged to move the support device 8 comprising the X-ray source 5, the collimators 7a-c, and the X-ray detector 6 along the z axis continuously to provide helical scanning or stepwise to provide rotational scanning at different z coordinates. Alternatively, the object is moved along the z axis to provide the helical scanning movement together with the rotation by the rotating device 10a.

Figure 2:
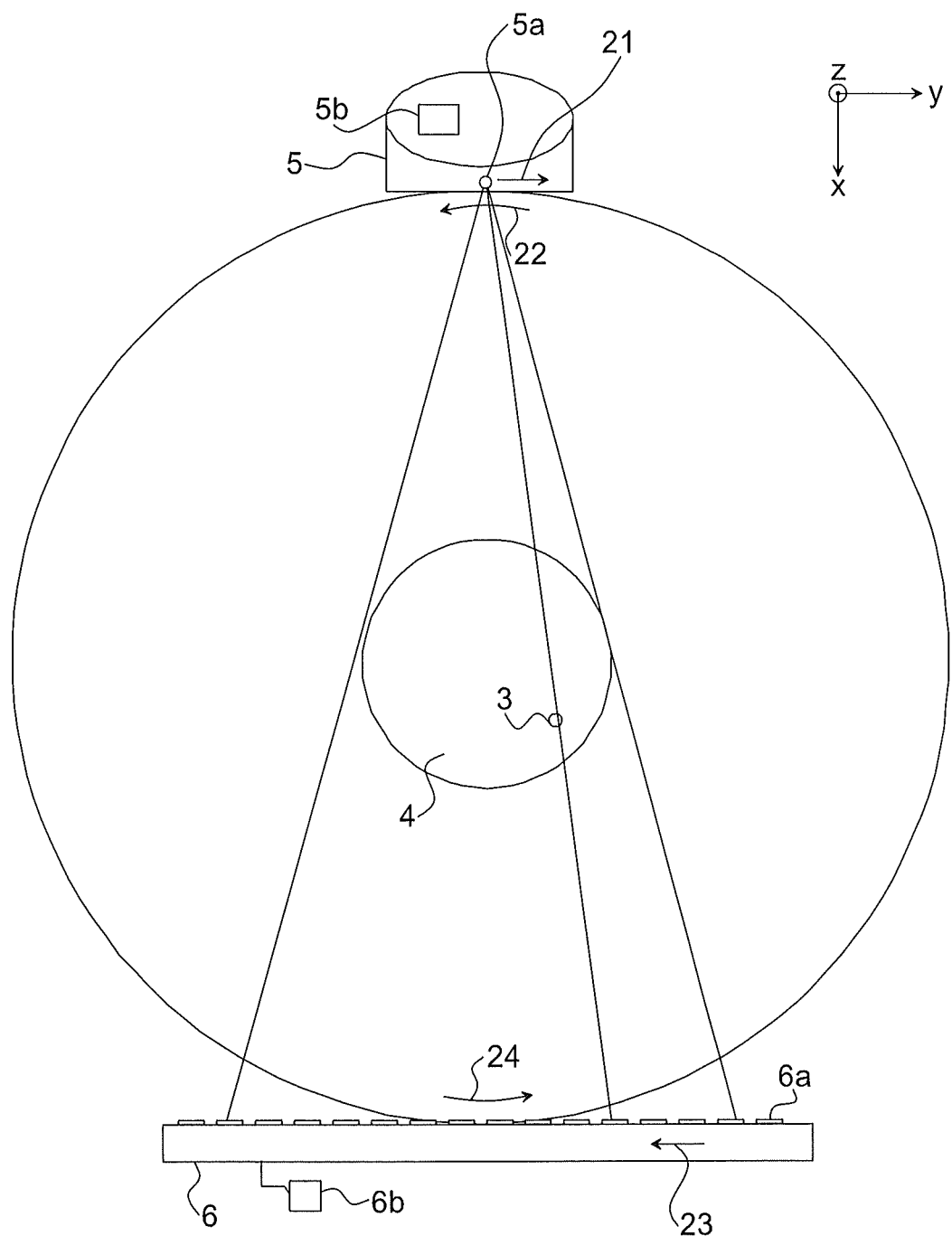
FIG. 2 illustrates schematically, in a top view, the X-ray source and the X-ray detector as being comprised in the computed tomography scanning system of FIG. 1.

The X-ray source 5 and the X-ray detector 6 are illustrated schematically in a top view in FIG. 2.

The X-ray source 5 comprises a flying focal spot 5a and means 5b for moving the flying focal spot 5a of the X-ray source 5 from an original position and in a direction 21 essentially opposite to the direction 22 the X-ray source 5 moves during the rotation by the rotating device 10a while the X-ray detector 6 records images. When the flying focal spot 5a has reached an end position it is quickly moved back to the original position while the X-ray detector 6 reads out signals.

The concept of flying focal spots is disclosed in the following publications: U.S. Pat. Nos. 6,256,369; and 5,841,829; and in references therein, the contents of all of which being hereby incorporated by reference.

The X-ray detector 6 comprises an array of pixels 6a arranged in at least one row for recording the images of the object, wherein the at least one row lies in the y direction and is thus perpendicular to the axis of rotation 12. The array may have between about 100 and 500 pixels, preferably between about 150 and 400 pixels, and more preferably between about 200 and 300 pixels, linearly arranged in the or each row. Each pixel is small and may measure between about 0.02 and 0.2 mm, preferably between about 0.05 and 0.15 mm, and most preferably not more than about 0.1 mm, in the y direction, and optionally in the z direction. The X-ray detector may have between about 10 and 500, preferably between about 25 and 250, and more preferably between about 50 and 150 rows of pixels arranged adjacent one another in the z direction.

It shall be appreciated that the X-ray detector 6 may comprise one or several above-mentioned one- or two-dimensional arrays of pixels in the yz plane. In particular, if large objects are to be scanned several arrays may be arranged linearly, one after the other, in the z direction. The X-ray detector 6 may be a solid state device such as a Cd—Te or Cd—Zn—Te based detector. Such kind of detector is disclosed in the following publications: U.S. Pat. Nos. 5,379,336; 6,933,505; 7,170,062; 7,189,971; 7,361,881; US 2006/011853; US2006/071174; and US2008/019477; and in references therein, the contents of all of which being hereby incorporated by reference.

Nevertheless, the present invention covers both photon counting devices as well as signal integrating devices.

Further, the X-ray detector includes means 6b for time delay integration (TDI) or summation such that pixel signal values of the at least one row of pixels 6a are shifted one pixel and summed with pixel signal values obtained in a following recording of an image, wherein the shifting and summing of pixel signal values are performed repeatedly. The pixel signal values are shifted in a direction 23 essentially opposite to the direction 24 the X-ray detector moves during the rotation by the rotating device 10a.

Various aspects of time delay integration or summation are disclosed in the following publications: U.S. Pat. Nos. 4,314,275; and 7,268,814; and in references therein, the contents of all of which being hereby incorporated by reference.

More in detail, the computed tomography image data are preferably recorded during a session comprising first longer recording periods and second shorter readout periods, wherein each first longer recording period is followed by a shorter second readout period. The length of each first longer recording period may be between about 100 µs and 10 ms, preferably between about 500 µs and 5 ms, and more preferably between about 500 µs and 1 ms, such as e.g. 900 µs. The length of each second shorter readout period may be between about 10 µs and 1 ms, preferably between about 50 µs and 500 µs, and more preferably between about 75 µs and 200 µs, such as e.g. 100 µs. Note that the TDI is only performed during each recording period, whereupon the TDI is referred to as partial TDI in contrast to normal TDI wherein TDI is performed and pixel values are readout continuously during the scan.

The rotating device 10a is provided for rotating the X-ray source 5 and the X-ray detector 6 at a certain rotational speed during both the first longer recording periods and second shorter readout periods. The rotational speed may preferably be between about 0.05 and 2 full revolutions per second, more preferably between about 0.1 and 1.5 revolutions per second, and most preferably between about 0.5 and 1 revolution per second. The rotation is made at least one half revolution, preferably at least one revolution, and most preferably between about 1 and 2 revolutions. Further, helical scanning may be performed.

During each first longer recording period the flying focal spot moving means 5b is provided for moving the flying focal spot 5a at a selected speed which is essentially equal to the circumferential speed of the X-ray source 5 due to the rotation by the rotating device 10a. This means that the flying focal spot is held still in space in a fixed position in space, e.g. "hovering" or being "freezed", during each first longer recording period. Given a distance of about 200 mm between the X-ray source 5 and the rotation axis 12 and a rotational speed of about 1 revolution per second, the selected speed of the flying focal point 5a would be about 1.2 m/s and the distance the 5a would be moved during each first longer recording period is about 1.1 mm if such period lasts for 900 µs.

Similarly, the time delay summation means 6b is, during each recording period, provided for shifting signal pixel values at a selected frequency, wherein the length of the pixels 6a in the direction of the row of pixels divided by the selected frequency of the shifting of consecutively recorded images is essentially equal to the circumferential speed of the X-ray detector 6 due to the rotation by the rotating device 10a. Hereby, the pixel value is shifted along the detector row with the same speed as the X-ray detector 6 moves and the summation of pixel signal values results in that the X-ray detector emulates an X-ray detector that is held still in space during each first longer recording period. Given a pixel length of about 0.1 mm and a distance of about 200 mm between the X-ray detector 6 and the rotation axis 12 the selected frequency of the shifting signal pixel values would be about 12 kHz or eleven shifts during each recording period of 900 µs.

The partial TDI is set up such that preferably between about 3 and 100 shifts, more preferably between about 5 and 50, and most preferably between about 5 and 20, such as e.g. 11, shifts are made during each recording period.

Figure 3:
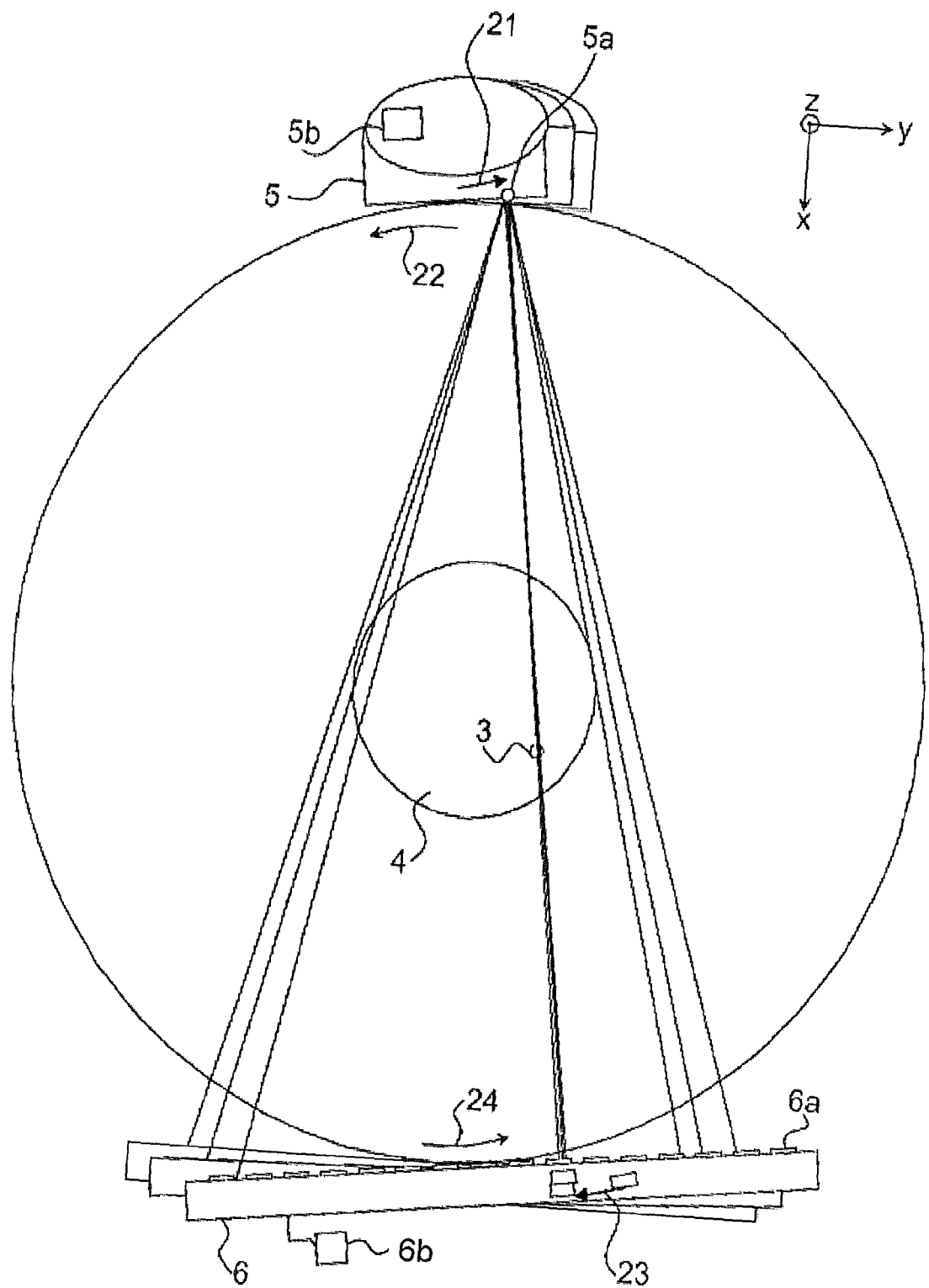
FIG. 3 illustrates schematically, in top views, the X-ray source and X-ray detector of FIG. 2 during three different instances of scanning in accordance with the principles of the invention.

FIG. 3 illustrates schematically, in top views, the X-ray source 5 and X-ray detector 6 of FIG. 2 during three different instances of scanning in accordance with the principles of the invention. The X-ray source 5 is moved in the direction of the arrow 22 and the X-ray detector 6 is moved in the direction of arrow 24. The opening angle of the radiation source 5a is indicated by the outermost radiation rays and further a radiation ray that passes through an object point 3 is indicated. As the X-ray source is moved in the direction of the arrow 22 the flying focal point 5a is moved in the opposite direction 21 such that the flying focal point 5a is essentially kept still. Concurrently, the pixel signal values are shifted in the direction of arrow 23, i.e. opposite to the direction (arrow 24), in which the X-ray detector 6 is moved, and pixel signal values are summed. As a result the summed signal value in a given pixel will essentially come from the radiation rays, which pass through the object point 3 in the same direction. The person skilled in the art notes that if scanning was performed with stepwise movement of the x-ray source 5 and X-ray detector 6, no smearing out of the signals would be obtained. However, continuous movement of the x-ray source 5 and X-ray detector causes some smearing out of the signal with a to some extent reduced spatial resolution as a result. However, the signal to noise ratio is improved a lot as compared to a similar apparatus without the flying focal spot 5a and the time delay integration/summation.

During each readout period no recording is preferably being made and the entire array of pixel values of the X-ray detector are readout, i.e. no shifting of pixel values is performed. Simultaneously, the flying focal spot moving means 5b is provided for moving the flying focal spot 5a back to its original position.

It should be noted that some edge effects will be obtained. If 11 shifts are made in the direction of arrow 23 in FIGS. 2-3, i.e. to the left, the 11 pixels most to the right of the row of pixels will have less than 12 integrated or summed pixel values (1 recorded pixel value and 11 shifted pixel values) in a decreasing number from left to right. The pixel most to the right will have only 1 pixel value recorded and none shifted. It shall be appreciated that some or all of these pixel values may be discarded in the CT reconstruction process. If some or all of them are used they will have to be normalized such that they can be compared to the pixel values of the more centrally and left-hand located pixels. Further, if being used in the CT reconstruction process after having been normalized, they can be less weighted than the pixel values of the more centrally and left-hand located pixels due to lower signal-to-noise ratio.

Further, it shall be noted that the pixel values shifted from the 11 pixels most to the left of the row of pixels in FIGS. 2-3 will have been shifted out of the row of pixel values during the recording period. These pixel values will have less than 12 integrated or summed values in an increasing number during the recording. Some or all of these pixel values may also be discarded in the CT reconstruction process. Alternatively, some or all of them are read out value by value (or column values by column values if the detector array has more than one row of pixels) and are normalized and optionally less weighted in the CT reconstruction process.

It shall be appreciated that the above effect will be similar for detector arrays having a plurality of detector rows.

If each row of pixels comprises 128 pixels, there will be 117 pixels with full signal levels (corresponding to 12 integrated or summed pixel values) and 11 plus 11 pixels with lower signal levels (corresponding to less than 12 integrated or summed pixel values).

It shall further be appreciated that since the X-ray detector does not record during each readout period there will be "black" stripes in the CT data. However, these will be narrow compared to the width of the CT data recorded during each recording period, since each recording period typically is many times longer than each readout period, e.g. at least about five or ten times longer.

The invention refers also to a mammography apparatus comprising the computed tomography scanning system.

It shall be appreciated that the various aspects and features of the invention as disclosed above may be combined in a plurality of different manners by a skilled person after having read the present description. The scope of protection of the present invention is given by the following claims.

The invention claimed is:

1. A computed tomography scanning system for recording computed tomography image data of an object in an object area comprising:
   an X-ray source and an X-ray detector arranged at either side of the object area, the X-ray source having a flying focal spot from which X-rays are emitted and the X-ray detector comprising pixels arranged in at least one row for recording images of the object, and
   a device provided for rotating said X-ray source and said X-ray detector with respect to said object around an axis of rotation which is substantially perpendicular to the at least one row of pixels, while the at least one row of pixels record images of the object, wherein
   the X-ray source comprises means for moving the flying focal spot of the X-ray source from an original position and in a direction essentially opposite to the direction the X-ray source moves during the rotation,
   said X-ray detector is provided with means for time delay summation such that pixel signal values of the at least one row of pixels are shifted one pixel and summed with pixel signal values obtained in a following recording of an image, wherein the shifting and summing of pixel signal values are performed repeatedly and the pixel signal values are shifted in a direction essentially opposite to the direction the X-ray detector moves during the rotation, and
   the means for moving the flying focal spot is provided for moving the flying focal spot and the means for time delay summation is provided for the repeated shifting and summing of pixel signal values during recurrent first periods of said rotation, after each of which first periods, during a second period of said rotation, the means for moving is provided for moving the flying focal spot back to its original position and the X-ray detector is provided for reading out the pixel signal values.

2. The system of claim 1 wherein the device for rotating is provided for rotating the X-ray source and the X-ray detector at a rotational speed and the means for moving is provided for moving the flying focal spot at a speed which is essentially equal to the circumferential speed of the X-ray source due to the rotation by the device for rotating.

3. The system of claim 2 wherein the means for time delay summation is provided for shifting pixel signal values at a frequency, wherein the length of the pixels in the direction of the row of pixels divided by said frequency is essentially equal to the circumferential speed of the X-ray detector due to the rotation by the device for rotating.

4. The system of claim 1 wherein each first period of said rotation is longer than each second period of said rotation.

5. The system of claim 1 wherein the X-ray detector comprises pixels arranged in a plurality of rows and the means for time delay summation is arranged such that pixel signal values of the plurality of rows of pixels are shifted and summed with pixel signal values obtained in a following recording of an image, wherein the shifting and summing of pixel signal values are performed repeatedly and the pixel signal values are shifted in a direction essentially opposite to the direction the X-ray detector moves during the rotation.

6. The system of claim 1 wherein the X-ray detector is a solid state detector.

7. The system of claim 6 wherein the solid state detector is a Cd—Te or Cd—Zn—Te based detector.

8. A mammography apparatus comprising the system of claim 1.

9. A method for recording computed tomography image data of an object in an object area by a computed tomography scanning system comprising an X-ray source and an X-ray detector arranged at either side of the object area, the X-ray source having a flying focal spot from which X-rays is emitted and the X-ray detector comprising pixels arranged in at least one row for recording images of the object and being equipped with time delay summation, the method being comprising the steps of:
   rotating said X-ray source and said X-ray detector with respect to said object around an axis of rotation which is substantially perpendicular to the at least one row of pixels, while
   recording images of the object by the at least one row of pixels
   moving the flying focal spot of the X-ray source from an original position and in a direction essentially opposite to the direction the X-ray source moves during the rotation, and shifting pixel signal values of the at least one row of pixels one pixel and summing the shifted pixel signal values with pixel signal values obtained in a following recording of an image, wherein the step of shifting and summing is performed repeatedly and the pixel signal values are shifted in a direction essentially opposite to the direction the X-ray detector moves during the rotation, wherein the flying focal spot is moved and the repeated step of shifting and summing is performed during recurrent first periods of the rotation, after each of which first periods, during a second period of said rotation, the flying focal spot is moved back to its original position and the pixel signal values are read out from the X-ray detector.

10. The method of claim 9 wherein said X-ray source and said X-ray detector are rotated at a rotational speed and the flying focal spot is moved at a speed which is essentially equal to the circumferential speed of the X-ray source due to the rotation of said X-ray source and said X-ray detector.

11. The method of claim 10 wherein pixel signal values of the at least one row of pixels are shifted at a frequency, wherein the length of the pixels in the direction of the row of pixels divided by said frequency is essentially equal to the circumferential speed of the X-ray detector due to the rotation of said X-ray source and said X-ray detector.

12. The method of claim 9 wherein each first period of said rotation is longer than each second period of said rotation.

13. The method of claim 9 wherein the X-ray detector comprises pixels arranged in a plurality of rows and signal pixel values of the at least one row of pixels are shifted and summed with pixel signal values obtained in a following recording of an image, wherein the shifting and summing of pixel signal values are performed repeatedly and the pixel signal values are shifted in a direction essentially opposite to the direction the X-ray detector moves during the rotation.

14. The system of claim 1 wherein each first period of said rotation is at least about five times longer than each second period of said rotation.

15. The method of claim 9 wherein each first period of said rotation is at least about five times longer than each second period of said rotation.

16. The system of claim 1 wherein each first period of said rotation is at least about ten times longer than each second period of said rotation.

17. The method of claim 9 wherein each first period of said rotation is at least about ten times longer than each second period of said rotation.

* * * * *